United States Patent
Dolan

(10) Patent No.: US 9,517,983 B2
(45) Date of Patent: Dec. 13, 2016

(54) REGENERATION LOOP CLEAN-UP

(71) Applicant: BASF Corporation, Florham Park, NJ (US)

(72) Inventor: William Dolan, Yardley, PA (US)

(73) Assignee: BASF CORPORATION, Florham Park, NJ (US)

(*) Notice: Subject to any disclaimer, the term of this patent is extended or adjusted under 35 U.S.C. 154(b) by 225 days.

(21) Appl. No.: 14/332,485

(22) Filed: Jul. 16, 2014

(65) Prior Publication Data

US 2016/0016865 A1 Jan. 21, 2016

(51) Int. Cl.
*C07C 7/13* (2006.01)
*B01D 53/04* (2006.01)

(52) U.S. Cl.
CPC ............ *C07C 7/13* (2013.01); *B01D 53/0423* (2013.01); *B01D 2253/104* (2013.01); *B01D 2253/108* (2013.01); *B01D 2256/24* (2013.01); *B01D 2257/30* (2013.01); *B01D 2257/504* (2013.01); *B01D 2257/70* (2013.01); *B01D 2259/4009* (2013.01); *B01D 2259/40086* (2013.01); *Y02P 20/142* (2015.11)

(58) Field of Classification Search
None
See application file for complete search history.

(56) References Cited

U.S. PATENT DOCUMENTS

| | | | |
|---|---|---|---|
| 4,479,814 A | 10/1984 | Oliker | |
| 4,484,933 A | 11/1984 | Cohen | |
| 4,971,606 A * | 11/1990 | Sircar | B01D 53/0462 |
| | | | 95/124 |
| 6,124,517 A | 9/2000 | Kaminsky et al. | |
| 7,326,821 B2 | 2/2008 | Risch et al. | |
| 8,147,588 B2 | 4/2012 | Dolan et al. | |
| 2014/0058083 A1* | 2/2014 | Rende | C07C 2/76 |
| | | | 540/485 |
| 2014/0330060 A1* | 11/2014 | Goris | C07C 2/12 |
| | | | 585/319 |

* cited by examiner

*Primary Examiner* — Tam M Nguyen
(74) *Attorney, Agent, or Firm* — Foley & Lardner LLP

(57) ABSTRACT

A process is disclosed for removing contaminants from an olefin stream, comprising passing the contaminated olefin stream through a first adsorbent in a thermal swing adsorption process to produce a relatively pure olefin product stream, and a regenerating gas stream containing the contaminants, passing the contaminated regenerating gas stream through a pressure swing adsorption process to yield a relatively pure regenerating gas stream, which can be redirected to the thermal swing adsorption process for regenerating the adsorbent therein.

19 Claims, 1 Drawing Sheet

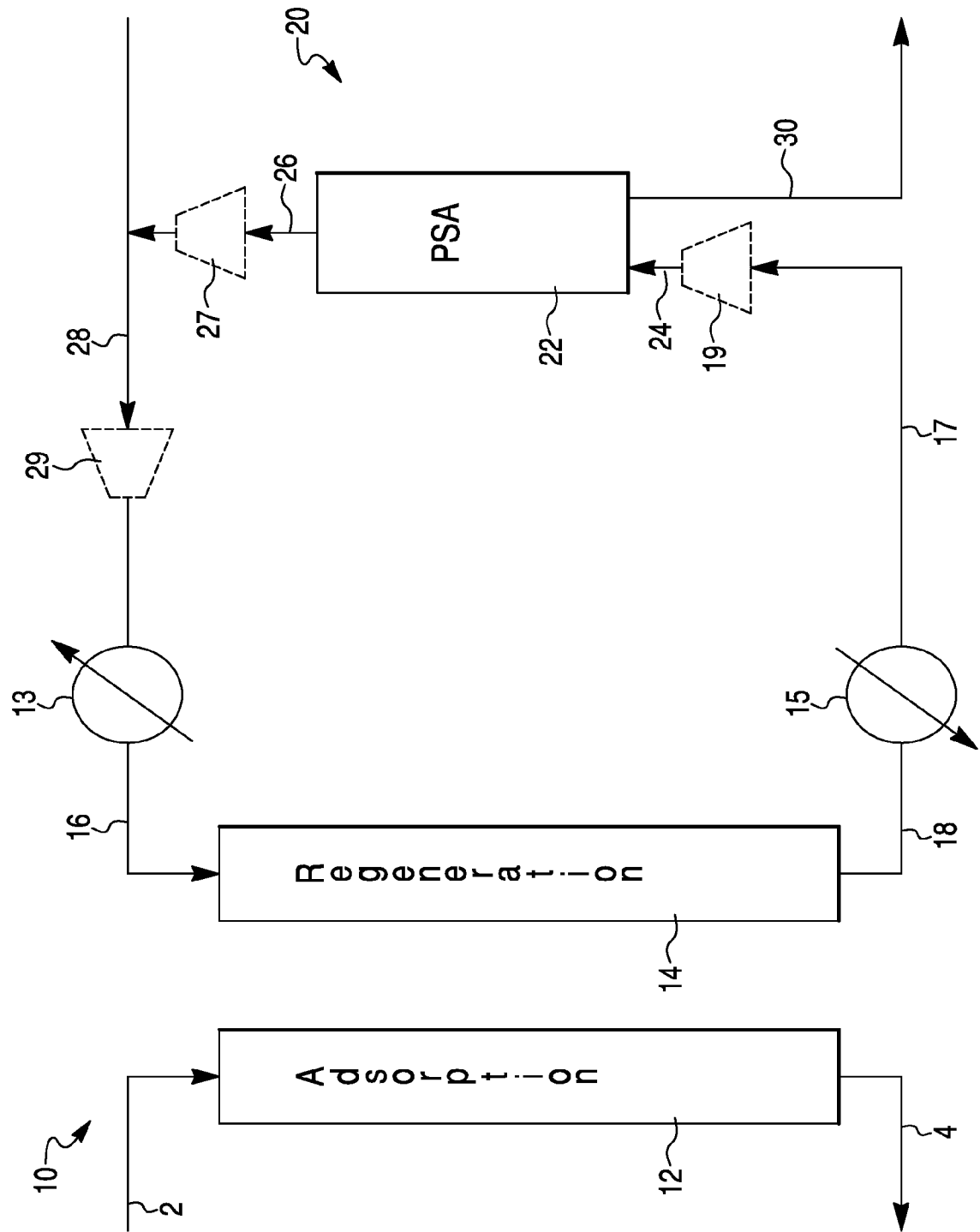

REGENERATION LOOP CLEAN-UP

FIELD OF THE INVENTION

The field of this invention relates to use of solid adsorbents in the purification of olefins. More particularly, this invention concerns purification by passing an olefinic process stream, containing small amounts of impurities, through a particulate adsorbent bed and regenerating the adsorbent in a manner which improves the efficiency of the purification process.

Processes according to this invention are particularly useful where the olefin being purified is ethylene and/or propylene.

BACKGROUND OF THE INVENTION

As is well known, olefins, or alkenes, are a homologous series of hydrocarbon compounds characterized by having a double bond of four shared electrons between two carbon atoms. The simplest member of the series, ethylene, is the largest volume organic chemical produced today. Importantly, olefins including ethylene, propylene and smaller amounts of butadiene, are converted to a multitude of intermediate and end products on a large scale, mainly polymeric materials.

Commercial production of olefins is accomplished by various methods including fluid catalytic cracking of hydrocarbons, stream cracking of hydrocarbons, e.g. alkanes, as well as dehydrogenation of alkanes, among other processes. Steam cracking of hydrocarbons is carried out using a feed which is ethane, propane or a hydrocarbon liquid ranging in boiling point from light straight-run gasoline through gas oil. Ethane, propane, liquid naphthas, or mixtures thereof are a preferred feed to a hydrocarbon cracking unit. Hydrocarbon cracking is generally carried out thermally in the presence of dilution steam in large cracking furnaces. Reaction conditions for steam cracking are selected to maximize the production of light olefins. Typically, cracking is practiced at a weight ratio of 0.3:1.0 of steam to hydrocarbon with the reactor outlet at 760°-870° C., and slightly above 100 kPa (atmospheric) pressure.

The type of feedstocks and the reaction conditions determine the mix of products produced. Many steam crackers operate on light paraffin feeds consisting of ethane and propane and the like. However, a significant amount of steam cracking capacity operates on feedstocks which contain propane and heavier compounds. Steam cracking such feedstocks tends to produce significant amounts of propylene, propane, butenes, and butadiene.

During steam cracking, cracked gases emerging from the reactors are rapidly quenched to arrest undesirable secondary reactions which tend to destroy light olefins. The cooled gases are subsequently compressed and separated to recover the various olefins.

The recovery of the various olefin products is usually carried out by fractional distillation using a series of distillation steps to separate out the various components. Generally, one of two basic flow sequences is used. The two sequences are usually denominated as the front-end depropanizer sequence, commonly referred to as 'front-end deprop', or the front-end demethanizer sequence, commonly referred to as 'front-end demeth'. Separation of the desired steam cracked olefin products from the overall product is known, and such separation processes do not form an aspect of this invention.

The manner in which the olefin stream to be purified by the invention is obtained is not critical to this invention, inasmuch as any hydrocarbon cracking method or dehydrogenation process typically forms an olefin stream that contains small amounts of impurities which can adversely affect further olefin processing such as polymerization.

For example, the separated olefins which are to be further used as a feed stream such as for polymerization, regardless of how formed, typically contain contaminants such as inorganic and organic sulfur-containing compounds, oxygenates, $CO_2$ and water, which must be removed to levels below about 1 ppm to avoid catalyst contamination and consequent reduction in activity and/or selectivity in the downstream processing of the purified olefin stream. The terms "contaminant" and "impurities" are meant to be interchangeable and denote minor components such as above described, which have an adverse effect on the downstream processing of an olefin stream.

U.S. Pat. No. 6,403,854 (Miller et al.) discloses removal of an oxygenate contaminant such as dimethyl ether from an olefin stream made by contacting methanol with a silicoaluminophosphate (SAPO) catalyst. The oxygenate contaminant is removed by cooling the olefin stream in a two stage quench process. In the first stage of the process, a substantial portion of the dimethyl ether is removed along with condensed water as a bottoms product. Additional dimethyl ether is removed in the second stage, and the olefin overhead is further treated for oxygenate removal by contacting with an adsorbent.

U.S. Pat. No. 7,326,821 discloses a highly efficient and relatively simple process for removing oxygenates, particularly dimethyl ether or acetaldehyde, more particularly dimethyl ether, from an olefin stream. The process uses a solid adsorbent to remove a majority of the oxygenates from the olefin stream. The adsorbent can retain relatively large quantities of oxygenate, while being substantially inert to converting desired olefin product to undesirable by-product.

Desirably, the solid adsorbent is a molecular sieve or metal oxide. Preferably, the solid adsorbent is a molecular sieve. The molecular sieve preferably has a framework structure of at least 8 rings. Also preferably, the molecular sieve is a zeolite. Particularly preferred zeolites include zeolite X, zeolite Y, ZSM-5, ZSM-11, ZSM-14, ZSM-17, ZSM-18, ZSM-20, ZSM-31, ZSM-34, ZSM-41 or ZSM-46. Of these, zeolite X or Y is preferred, with zeolite X being particularly preferred.

The solid adsorbent can be kept in continuous use by regenerating the adsorbent following contact with the provided olefin stream. Regeneration of the solid adsorbent can be carried out by any conventional method. Such methods include treatment with a stream of a dry inert gas such as nitrogen at elevated temperature (temperature swing adsorption or TSA). In the regeneration stage, a regenerant comprising a hot fluid is passed along the flow path in a co-current, or more commonly, a countercurrent direction. The high temperature of the regenerant produces a desorption front in the bed which drives the sorbate from the sorbent material and into the flowing regenerant stream. This process continues until the bed is substantially sorbate-free, typically as indicated by the emergence of hot regenerant fluid at the bed exit.

In such TSA processes, the heated stream leaving the adsorbent, and which contains the desorbed contaminants is then either sent to a fuel header (if methane) or flare (if nitrogen). If nitrogen is used as the regeneration gas, then that nitrogen has a direct value, and if it were possible to recover a portion of that nitrogen, it would be valuable as nitrogen demand could be reduced by recycle of purified nitrogen back to the unit. Alternatively, if methane is used as the regeneration gas, there is value in purifying it also for reuse, as many steam cracking plants, especially those that use ethane as a primary feed component, do not generate sufficient amounts of methane for use in regenerating TSA purification systems.

SUMMARY OF THE INVENTION

A process is disclosed for the thermal regeneration of an adsorbent containing one or more contaminants adsorbed from an olefin stream by a TSA process. The process comprises passing at an elevated regeneration temperature an inert regeneration gas which is essentially free of the contaminants through a bed of the adsorbent, which initially contains the adsorbed contaminants, whereby the adsorbed contaminants are desorbed, withdrawing from the adsorbent bed a purge effluent stream comprising desorbed contaminants and the inert regeneration gas, and passing the purge effluent stream through an adsorbent at elevated pressure to adsorb the contaminants from the purge effluent stream and produce a pure inert regeneration gas stream. The essentially contaminant-free regeneration gas stream can be used or combined with makeup regeneration gas, for desorption in the thermal swing adsorption process.

BRIEF DESCRIPTION OF THE DRAWINGS

The FIGURE is a schematic flow diagram of the process of the present invention, illustrating the flow of feed to a TSA system and the use of a PSA system for cleaning the regeneration gas for reuse in the TSA system.

DETAILED DESCRIPTION OF THE INVENTION

This invention provides a process for removing contaminants, for example, sulfur-containing compounds including mercaptans, organic sulfides and disulfides such as COS and $CS_2$, and inorganic sulfides such as $H_2S$, organic oxygenates such as ethers, esters, aldehydes, alcohols, $CO_2$ and water, from an olefin stream. In general, the process comprises providing an olefin stream that contains contaminants, and then removing a majority (i.e., greater than 50%) of the contaminants present in the olefin stream in a thermal swing or TSA processing system.

In this invention, a solid adsorbent is used for removing the contaminants from the olefin stream. The particular solid adsorbent has the characteristics of high contaminant adsorption capacity and low cumulative oligomer selectivity. That is, the solid adsorbent has the ability to adsorb a substantial amount of contaminants from the olefin stream, and is essentially inert in that it has low or no activity in converting olefins in the olefin stream to other products such as olefin dimers, oligomers or polymers (collectively referred to as oligomers). The end result in using the solid adsorbent of this invention is that the adsorbent can remove contaminants, including organic oxygenates such as dimethyl ether or acetaldehyde, and others as noted previously, from an olefin stream down to a very low level. In addition, the adsorbent can hold a significant quantity of the adsorbed material, and the adsorbent does not significantly deplete the desired olefin product in the olefin stream by causing the olefin to be converted to the undesirable oligomer by-products.

In one embodiment of the invention, the solid adsorbent is a molecular sieve. Molecular sieve materials all have 3-dimensional, four-connected framework structure of corner-sharing $TO_4$ tetrahedra, where T is any tetrahedrally coordinated cation, such as aluminum. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., Introduction to Zeolite Science and Practice, Second Completely Revised and Expanded Edition, Volume 137, pages 1-67, Elsevier Science, B. V., Amsterdam, Netherlands (2001).

The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å.

The molecular sieves can be amorphous, crystalline, or a combination thereof. Examples include zeolite as well as non-zeolite molecular sieves, which are of the large, medium or small pore type. Non-limiting examples of these molecular sieves include the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Preferred types of molecular sieves include faujasites, pentasils, mordenite, beta, VPI, MCM, and substituted aluminophosphates such as SAPO, MeAPO, ELAPO, and ELAPSO. Non-limiting examples of the preferred molecular sieves include zeolite X, zeolite Y, zeolites 3A, 4A, 5A, 13X, VPI-5, MCM-41, ZSM-5, ZSM-11, ZSM-14, ZSM-17, ZSM-18, ZSM-20, ZSM-31, ZSM-34, ZSM-41 and ZSM-46. In one embodiment, the molecular sieve of the invention is zeolite X or zeolite Y, including zeolite 13X, as well as aluminas or composites of alumina with zeolite X or zeolite Y. Excess soda may also be added in addition to the adsorbents to reduce reactivity of the olefin component as disclosed in commonly assigned U.S. Pat. No. 8,147,588 to Dolan, et al.

The olefin stream from which the contaminant is separated according to this invention can be provided from any conventional source. Such olefin streams can be provided, for example from, cracking of petroleum streams, catalytic reaction of contaminants to form olefins, or dehydrogenations of hydrocarbons.

This invention is particularly beneficial in, although not to be limited to, removing contaminants from olefin streams made in the process of thermal cracking of hydrocarbons. The olefin stream is one that is formed by such process or any known process and has been treated to remove unwanted products including $C_2$-$C_4$ alkanes, $C_{5+}$ products, etc., such as described in U.S. Pat. No. 5,090,977, which is intended to be one example of such process that can be used. In the separated olefin streams which result, contaminants such as organic oxygenates, inorganic and organic sulfur-containing compounds, $CO_2$ and water can be present in minor concentrations. The presence of such contaminants, even in small concentrations, can cause problems in further processing the olefins (particularly ethylene and/or propylene) from these streams. For example, these contaminants can poison many conventional polyethylene and polypropylene forming catalysts.

In one embodiment of the invention, the olefin stream from which the contaminants are to be removed comprises not greater than about 500 wppm contaminants, preferably not greater than about 50 wppm contaminants, based on total weight of the olefin stream. Of course, for contaminants to be removed from the olefin stream, some measurable amount must be present. In one embodiment, the provided olefin stream will contain at least about 0.1 ppm contaminants; and in another, at least about 1 ppm contaminants, based on total weight of the olefin stream.

In particular, the olefin stream which is treated in accordance with this invention, contains ethylene, propylene, butylene, or a combination thereof. Desirably, the olefin stream contains at least about 50 wt. % ethylene, propylene, butylene, or a combination thereof, based on total weight of the olefin stream. Preferably, the olefin stream contains from about 50 wt. % to about 99+ wt. % ethylene, propylene, butylene, or a combination thereof, more preferably from about 90 wt. % to about 99+ wt. % ethylene, propylene, butylene, or a combination thereof, based on total weight of the olefin stream.

In the process of the invention, the contaminated olefin stream to be purified contains one or more contaminants, more specifically, one or more organic compound(s) containing at least one oxygen atom. Thus, the contaminants include one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. Other contaminants include sulfur compounds, such as $H_2S$, mercaptans, sulfides and disulfides as previously mentioned, $CO_2$ and water.

In this invention, removal or adsorption of the contaminants from the olefin stream is accomplished using one or more adsorption beds. The beds can be arranged in series or parallel, and can be any type of conventional bed system. The adsorption beds can be operated at ambient temperatures or at elevated temperatures as required. Flow of the olefin stream through the beds can be either upward or downward. The adsorption process is carried out in the gas phase.

The temperature at which the provided olefin stream is contacted with the solid adsorbent can vary over a wide range. In one embodiment, the provided olefin stream is contacted with the solid adsorbent in the gas phase at a temperature of from about 0° C. to about 100° C.

The pressure at which the provided olefin stream is contacted with the solid adsorbent can also vary over a wide range. In one embodiment, the provided olefin stream is contacted with the solid adsorbent at a pressure of from about 0.01 psig to about 500 psig.

Space velocity at which the provided olefin stream is contacted with the solid adsorbent can vary widely. For example, in one embodiment in the gas phase, the provided olefin stream is contacted with the solid adsorbent at a gas hourly space velocity (GHSV) of from about 100 $hr^{-1}$ to about 20,000 $hr^{-1}$.

In one embodiment of the invention, a majority of the contaminants present in the provided olefin stream are removed from the olefin stream. In particular, the level of contaminants remaining in the purified olefin stream should be less than 10 ppm and, more preferably, less than 1 ppm.

In this invention, the solid adsorbent is regenerated with a heated purge gas following contact with the provided olefin stream. It is preferable to regenerate the solid adsorbent before the adsorbent reaches full adsorption capacity. That is, it is preferred to regenerate the solid adsorbent just before it becomes fully saturated. At full saturation, breakthrough of the contaminant occurs, meaning that contaminants are no longer adsorbed from the olefin stream, and that the adsorbent is essentially ineffective in operation.

During the regeneration of a primary adsorbent bed, the purge gas is heated to temperatures significantly higher than the temperature of the adsorbent mass, in order to lower the equilibrium impurity loading and facilitate desorption and purging of the impurity adsorbates from the bed. In general, the higher the purge gas temperature, the less the quantity of purge gas required, although such factors as hydrothermal abuse of the adsorbent and higher heat energy losses due to untoward differentials between internal and external bed temperatures will be taken into account by those skilled in the art. It is not necessary that the purge gas be heated over the entire period of the hot purge regeneration, since the heat of the regenerated adsorbent mass at the ingress end of the bed during regeneration can be carried forward even with unheated incoming purge gas, but the primary bed at the end of the regeneration stage will advantageously contain sufficient heat energy so that upon the following cool-down purge, the effluent purge gas is capable of regenerating the auxilliary adsorbent bed. Factors which determine the accomplishment of this result include the relative size of the primary bed and the impurity loading of the bed. Routine calculations are readily made in view of any given process system to establish suitable process conditions. In one embodiment of the invention, the solid adsorbent is regenerated at a temperature of from about 200° C. to about 500° C.

The pressure at which the regeneration takes place is also favorable for effective removal of contaminants, preferably at a temperature at which the contaminants are desorbed from the pore structure of the adsorbent, particularly from the pore structure of a molecular sieve adsorbent. In one embodiment, the solid adsorbent is regenerated at a pressure of from about 0.01 psig to about 400 psig.

In this invention, an inert medium is used to sweep the adsorbent during the regeneration process to aid in removing the contaminants within the pore structure. The gas hourly space velocity (GHSV) during regeneration is not critical and can vary widely. In one embodiment, the solid adsorbent is regenerated at a gas hourly space velocity of from 10 $hr^{-1}$ to 5,000 $hr^{-1}$.

The non-adsorbable purge gas or inert medium employed can be any of those commonly used in other adsorption-separation processes and include hydrogen, nitrogen, helium, argon and the other inert gases and fuel gas defined as hydrogen, methane, higher alkanes or mixtures thereof. It will be understood that the term "non-sorbable purge gas" is used in its relative sense and includes materials which may have some degree of affinity for molecular sieves, but which are easily displaced from the adsorbent by any impurity of the feedstock which is desired to be removed. In accordance with this invention, most useful purge gases used include fuel gas as above defined or nitrogen to regenerate the adsorbent. The nitrogen and fuel gas streams for regeneration are essentially pure streams containing at least 99 wt. % of the desired gas.

In a typical practice of regenerating an adsorbent used in purifying an olefin stream, the nitrogen or fuel gas purge, subsequent to passing through the adsorbent and ladened with the desorbed impurities is simply burned. Unfortunately, burning nitrogen with the contaminants poses atmospheric pollution problems and typically requires the issuance of permits from affected municipalities to operate. In addition, the value of the nitrogen is lost and there is a significant cost in continually replenishing the nitrogen regenerating gas stream. Likewise, the burning of fuel gas including methane or other alkanes increases greenhouse gas emissions. Moreover, if the olefin stream is formed by a thermal cracking process, a significant amount of ethane is present in the feed stream, and sufficient methane is not produced. As such, makeup methane needs to be provided for regeneration, again adding to the cost of the process.

Accordingly, in this invention, the purged regeneration gas, subsequent to desorbing the impurities from the adsorbent in the TSA system is passed through an adsorbent bed which removes the impurities from regeneration gas and allows the regeneration gas to be reused to regenerate the TSA adsorbent. Thus, the impurity-ladened regeneration gas is passed through an adsorbent at elevated pressure, so as to result in the adsorption of the impurities and yield a product regeneration gas essentially free of the impurities. This adsorption system for recovering a purified regenerating gas operates on a pressure swing, such that the adsorbent itself is regenerated by reducing the pressure and causing the impurities to be desorbed from the adsorbent. Any of the adsorbents used in the TSA process as exemplified above can be used in the pressure swing or PSA process to remove the impurities from the regeneration gas. Preferably, however, the adsorbent in the PSA system is a weaker adsorbent with respect to the impurities relative to the sorbate attraction of adsorbent in the TSA system, and would be less reactive toward the olefins. A preferred adsorbent in the PSA system for removing the impurities from the nitrogen or fuel gas regeneration gas is alumina.

A further understanding of the process of this invention can be derived from an explanation of the FIGURE, which illustrates the combined process of this invention for reducing the impurities in an olefin stream, and the continual reuse of a regenerating gas as above described. Referring to the FIGURE, reference numeral 10 refers to the TSA system used to remove impurities from an olefin stream, whereas reference numeral 20 refers to a PSA system used to clean and remove impurities from the regeneration gas for reuse in TSA system 10. TSA system 10 includes one or more adsorption units or columns filled with a solid particulate adsorbent (not shown) as exemplified previously and, which preferably, is an alumina zeolite composite as disclosed in previously mentioned U.S. Pat. No. 8,147,588, the entire disclosure of which is herein incorporated by reference.

As disclosed in U.S. Pat. No. 8,147,588, a solid shaped adsorbent is provided comprising an alumina component, a zeolite component and an added metal component selected from, for example, the group consisting of alkali metals, alkaline earth metals and mixtures thereof, the added metal component being initially added primarily to the zeolite component such that the amount of added metal is greater in the zeolite than if the same amount of initial metal was added to a mixture of the zeolite and alumina. The added metal component is present in an amount over the stoichiometric amount of metal needed to compensate for the negative charge of the zeolite lattice.

Activated aluminas include aluminas having a surface area usually greater than 100 m²/g and typically in the range of 100 to 400 m²/g. Further, the activated alumina powder is preferably obtained by rapid dehydration of aluminum hydroxides, e.g., alumina trihydrate of hydrargillite in a stream of hot gasses or solid heat carrier. Dehydration may be accomplished in any suitable apparatus using the stream of hot gases or solid heat carrier. Generally, the time for heating or contacting with the hot gases is a very short period of time, typically from a fraction of a second to 4 or 5 seconds. Normally, the temperature of the gases varies between 400° and 1000° C. The process is commonly referred to as flash calcination and is disclosed, for example in U.S. Pat. No. 2,915,365, incorporated herein by reference. However, other methods of calcination may be employed.

The activated aluminas suitable for use in the present invention have a median particle size in the range of 0.1 to 300 microns, preferably 1 to 100 microns and typically 1 to 20 microns. In certain instances, it may be desirable to use aluminas with a median particle size of 1 to 10 microns. The alumina may be ground to the desired particle size before or after activation. The activated alumina typically has an LOI (loss on ignition) in the range of about 5 to 12% at a temperature of 200° to 1000° C.

One source of activated alumina is gibbsite which is aluminum trihydrate derived from bauxite using the Bayer process. However, alpha alumina monohydrate, pseudoboehmite or other alumina trihydrates may be used if sufficiently calcined. Other sources of alumina may also be utilized including clays and aluminum alkoxides.

Zeolites are crystalline aluminosilicate compositions which are microporous and have a three-dimensional oxide framework formed from corner sharing $AlO_2$ and $SiO_2$ tetrahedra. Zeolites are characterized by having pore openings of uniform dimensions, having a significant ion exchange capacity, and being capable of reversibly desorbing an adsorbate dispersed throughout the internal voids of the crystal without significantly displacing any atoms which make up the permanent zeolite crystal structure. The zeolites which can be used in the present invention are those which have a pore opening of about 5 to about 10 Å.

In general, the zeolites have a composition represented by the empirical formula:

$$M_{2/n}O:Al_2O_3bSiO_2$$

M is a cation having a valence of "n" and "b" has a value of about 2 to about 500. Preferred zeolites are those that have a $SiO_2/Al_2O_3$ ratio of about 2:1 to about 6:1 and/or those having the crystal structure of zeolite X, faujasite, zeolite Y, zeolite A, mordenite, ZSM-5, beta and ferrierite. Especially preferred zeolites are zeolites X, Y and A.

A particularly useful component of the shaped adsorbent is an added metal component selected from the group consisting of alkali, alkaline earth metals and mixtures thereof. This added metal component is in addition to the metal cation (M) present in the exchange sites of the zeolite. The added metal can be the same or different than the M metal.

Specific examples of added metal include but are not limited to sodium, potassium, lithium, rubidium, cesium, calcium, strontium, magnesium, barium, zinc and copper. The source of the added metal (metal component precursor) can be any compound which at activation conditions, (see infra) decomposes to the metal oxide. Examples of these sources are the nitrates, hydroxides, carboxylates, carbonates and oxides of the metals.

The shaped adsorbent can be prepared by combining the three components in an order which provides an amount of the added metal component in the zeolite in an amount greater than if the same amount of metal was added to a mixture of the zeolite and alumina. Methods of preparation to intentionally contact the alumina with the added metal are preferably avoided such that only the zeolite is treated to contain the metal and, therefore, only the zeolite should contain the added metal during initial processing. However, during the forming process as described below, it is inevitable that some quantity of added metal will migrate to the alumina. The final product, however, will be such that the amount of added metal component in the zeolite is greater than if the same amount of initial metal was contacted with a mixture of zeolite and alumina. Particular methods of forming the alumina-zeolite composite are described in the aforementioned patent.

The individual adsorption units each operate in a cycle of adsorption, desorption and regeneration, and cooling. Reference numerals 12 and 14 represent the adsorption units in the adsorption and regeneration cycles, respectively. In the adsorption unit 12, an olefin feed 2 is passed through one end of the unit to the other, so that the feed gas passes through the adsorbent and an olefin product 4 leaves unit 12 at the opposite end of unit 12 receiving the feed. Product 4 is substantially free of any impurities. As shown in the FIGURE, during the regeneration cycle, a nitrogen or fuel gas feed 16 is directed to unit 14 which contains an impurity-ladened adsorbent (not shown), and exits via line 18 containing the desorbed impurities from the adsorbent in the unit 14. The regeneration gas prior to entering regeneration unit 14 can be heated by heater 13, or from heat during compression in compressor 29, to the proper temperature for heating the adsorbent and facilitating the desorption of the impurities from the adsorbent. Once the regeneration gas containing the impurities leaves unit 14, the gas is cooled and water condensed in cooler-knock-out unit 15 and can then be directed to a compressor 19, if needed, via line 17, for treatment in PSA system 20. Heating and/or cooling as described above can also be achieved by heat exchange with any of the process streams as appropriate.

The PSA system 20 also includes an adsorbent unit 22, filled with a particulate adsorbent (not shown). Similar to the TSA system, each bed or unit of the PSA system operates on a sequential pressurization/adsorption and a depressurization/regeneration cycle. PSA processes are typically carried out in multi-bed systems as illustrated in U.S. Pat. No. 3,430,418 to Wagner, which describes a system having at least four beds. As is generally known and described in this patent, the PSA process is commonly performed in a cycle of a processing sequence that includes in each bed: (1) higher pressure adsorption with release of product effluent from the product end of the bed; (2) co-current depressurization to intermediate pressure with release of void space gas from the product end thereof; (3) countercurrent depressurization to a lower pressure; (4) purge; and (5) pressurization. The void space gas released during the co-current depressurization step is commonly employed for pressure equalization purposes and to provide purge gas to a bed at its lower desorption pressure. Suitable adsorbent materials include materials based on alumina or silica-alumina and zeolite type adsorbents. In general, inlet temperatures of the PSA adsorption stage can range from about 25 to 270° C., preferably about 25-200° C., and 50 to 150° C. is also exemplified. Inlet pressures of 50 to 500 psia, preferably 50 to 250 psia, and further exemplified by 50 to 150 psia can be used.

Shown in the FIGURE is adsorption unit 22, which represents both the adsorption and desorption stages. Again, referring to the FIGURE, the regeneration gas now ladened with impurities leaving TSA system 10, and at operational pressure, passes to the PSA adsorbent unit 22 via line 24. At the opposite end of unit 22 from which the feed enters via line 24 is a clean regeneration gas free of impurities leaving via line 26. A portion or all of the clean regeneration gas via line 26 can be heated as above described and used to regenerate the TSA adsorbent bed 14 via line 16, where the clean regeneration gas can again be used to desorb the impurities from the adsorbent in unit 14 in TSA 10, and the cycle begins again. Operational pressure for the PSA system 20 can be achieved by one or more compressors 19, 27 and 29 connected to lines 17, 26, and 28, respectively. The PSA system 20 includes a regeneration cycle, in which at low pressure, e.g. 5-30 psia, preferably 15-25 psia, the impurities from the regeneration gas are desorbed from the adsorbent in unit 22, and leaves as a reduced pressure waste gas via line 30. It is particularly useful if the ratio of adsorption pressure to desorption pressure is at least 2.0. Thus, in accordance with this invention, the regeneration gas used to regenerate the TSA system 10 is not wasted, but can be continuously reused with greatly reduced amounts of makeup regenerating purge gas required. The reduction, if not elimination of burning the impurity-ladened regeneration gas, also reduces the costs required for the permitting process needed to burn such materials and can result in significantly reduced pollution issues.

The ethylene and/or propylene streams treated according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene and/or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_{4+}$ olefins, particularly butylene, treated according to this invention. The olefins treated according to this invention can also be used in the manufacture of such compounds as aldehydes, acids such as $C_2$-$C_{13}$ mono carboxylic acids, alcohols such as $C_2$-$C_{12}$ mono alcohols, esters made from the $C_2$-$C_{12}$ mono carboxylic acids and the $C_2$-$C_{12}$ mono alcohols, linear alpha olefins, vinyl acetate, ethylene dichloride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_{4+}$ olefins, butylene in particular, are particularly suited for the manufacture of aldehydes, acids, alcohols, esters made from $C_5$-$C_{13}$ mono carboxylic acids and $C_5$-$C_{13}$ mono alcohols and linear alpha olefins.

The invention claimed is:

1. A process for removing contaminants from an olefin feed comprising:
   a) directing said olefin feed into contact with a first particulate adsorbent bed capable of removing said contaminants from said olefin feed, and producing an olefin product containing less contaminants than said feed;
   b) heating said first adsorbent bed and directing a regenerating gas through the first adsorbent bed to desorb said contaminants from said adsorbent, and produce a regeneration gas effluent containing said contaminants; and
   c) directing said regeneration gas effluent through a second particulate adsorbent bed, so as to adsorb and remove said contaminants from said regeneration gas effluent and produce a regenerating gas product having a reduced level of contaminants than said regeneration gas effluent;
   wherein said contaminants comprise organic oxygenates, inorganic sulfur compounds, organic sulfur compounds, or a mixture thereof.

2. The process of claim 1, wherein said first particulate adsorbent bed comprises an alumina, a zeolite, a composite of alumina-zeolite, or alumina, zeolite, or composite of alumina-zeolite doped with an oxide of alkali or alkaline-earth metals.

3. The process of claim 2, wherein said first adsorbent bed comprises zeolite 3A, 4A, 5A, 13X or Na Y or combinations of said zeolites with alumina.

4. The process of claim 1, wherein said regenerating gas is nitrogen or fuel gas.

5. The process of claim 1, wherein said contaminants comprise organic oxygenates.

6. The process of claim 1, wherein said contaminants comprise inorganic sulfur compounds or organic sulfur compounds.

7. The process of claim 1, wherein said contaminants comprise up to 500 ppm of said olefin feed.

8. The process of claim 1, comprising desorbing the contaminants from said second adsorbent bed by reducing the pressure in said second adsorbent bed and form a low pressure waste gas containing said contaminants.

9. The process of claim 8, wherein said second adsorbent bed comprises alumina.

10. The process of claim 1, wherein said regenerating gas effluent containing said contaminants is cooled prior to contact with said second particulate adsorbent.

11. The process of claim 10, wherein water is removed from said regenerating gas effluent during said cooling.

12. The process of claim 1, wherein said first adsorbent bed is heated by heating said regenerating gas and passing said regenerating gas in contact with said first adsorbent bed.

13. The process of claim 12, wherein said regenerating gas is heated to a temperature of from about 200-500° C.

14. The process of claim 1, wherein said regenerating gas effluent containing said contaminants is pressurized to a pressure of at least 50 psia prior to contact with said second adsorbent bed.

15. The process of claim 1, wherein the ratio of adsorption pressure to desorption pressure in said second adsorption bed is at least 2.0.

16. The process of claim 1, comprising directing at least a portion of said regenerating gas product to said first adsorbent bed containing adsorbed contaminants.

17. The process of claim 1, wherein said olefin feed stream contains at least about 50 wt. % ethylene, propylene, butylene, or a mixture thereof.

18. The process of claim 17, wherein said olefin feed stream comprises at least 90 wt. % of ethylene, propylene, butylene, or a mixture thereof.

19. The process of claim 16, wherein said regenerating gas is nitrogen or fuel gas.

* * * * *